(12) United States Patent
Haslem

(10) Patent No.: US 12,173,483 B1
(45) Date of Patent: Dec. 24, 2024

(54) SOLAR POWERED WATER COLLECTION, TREATMENT AND DISPENSER SYSTEM

(71) Applicant: Stephen Haslem, Los Angeles, CA (US)

(72) Inventor: Stephen Haslem, Los Angeles, CA (US)

(*) Notice: Subject to any disclaimer, the term of this patent is extended or adjusted under 35 U.S.C. 154(b) by 479 days.

(21) Appl. No.: 17/462,984

(22) Filed: Aug. 31, 2021

Related U.S. Application Data

(60) Provisional application No. 63/074,272, filed on Sep. 3, 2020.

(51) Int. Cl.
| | |
|---|---|
| *E03B 3/00* | (2006.01) |
| *A61L 9/20* | (2006.01) |
| *C02F 1/44* | (2023.01) |
| *E03B 3/28* | (2006.01) |

(52) U.S. Cl.
CPC ............ *E03B 3/28* (2013.01); *A61L 9/20* (2013.01); *C02F 1/441* (2013.01); *A61L 2209/14* (2013.01); *C02F 2201/008* (2013.01); *C02F 2201/009* (2013.01)

(58) Field of Classification Search
CPC .................... C02F 1/441; E03B 3/28
See application file for complete search history.

(56) References Cited

U.S. PATENT DOCUMENTS

| | | |
|---|---|---|
| 5,845,504 A | 12/1998 | LeBleu |
| 6,588,226 B1 | 7/2003 | Semrow et al. |
| 6,755,037 B2 | 6/2004 | Engel et al. |
| 6,868,690 B2 | 3/2005 | Faqih |
| 6,869,464 B2 | 3/2005 | Klemic |
| 6,945,063 B2 | 9/2005 | Max |
| 7,337,615 B2 | 3/2008 | Reidy |
| 7,373,787 B2 | 5/2008 | Forsberg et al. |
| 7,866,176 B2 | 1/2011 | Vetrovec et al. |
| 8,607,583 B2 | 12/2013 | Morgan et al. |
| 8,627,673 B2 | 1/2014 | Hill et al. |
| 9,400,124 B2 | 7/2016 | Ferreira et al. |
| 9,587,381 B2 | 3/2017 | Turner, Jr. |
| D795,629 S | 8/2017 | Ullman |
| D837,735 S | 1/2019 | Marcille et al. |
| 10,525,373 B2 | 1/2020 | Dorfman |

(Continued)

FOREIGN PATENT DOCUMENTS

| | | |
|---|---|---|
| CH | 710469 | 6/2016 |

*Primary Examiner* — Eric S Ruppert
(74) *Attorney, Agent, or Firm* — John Rizvi; John Rizvi, P A—The Patent Professor®

(57) ABSTRACT

A solar powered water collection, treatment and dispenser system condenses water from surrounding moisture laden air. The system includes a housing assembly having at least one solar collection panel mounted thereto to generate electrical power to operate the system. A collection assembly has an air intake unit to draw in the surrounding moisture laden air and a dehumidifier to condense untreated water from the moisture laden air drawn into the system. A reverse osmosis assembly remove contaminants from the untreated water to produce treated water. Hot and cold water assemblies are provided having a heated water tank and a cooled water tank, respectively, to receive treated water from the reverse osmosis assembly, and to dispense hot and cold treated water to the user therefrom via hot and cold water dispensers.

14 Claims, 12 Drawing Sheets

(56) References Cited

U.S. PATENT DOCUMENTS

| | | |
|---|---|---|
| 10,619,332 B2 | 4/2020 | Rockenfeller et al. |
| 2007/0261162 A1* | 11/2007 | Atkinson ................. E03B 1/04 |
| | | 4/625 |
| 2007/0295021 A1 | 12/2007 | Tyls et al. |
| 2008/0276630 A1* | 11/2008 | Lukitobudi ............ B01D 5/009 |
| | | 62/93 |
| 2009/0077992 A1 | 3/2009 | Anderson et al. |
| 2012/0073320 A1 | 3/2012 | Seoane |
| 2013/0220906 A1 | 8/2013 | Stenhouse |
| 2014/0262989 A1* | 9/2014 | Pimentel ............... B01D 61/12 |
| | | 210/96.2 |
| 2014/0305787 A1 | 10/2014 | Nguyen |
| 2015/0336048 A1 | 11/2015 | Goelet |
| 2018/0106509 A1* | 4/2018 | Hollingsworth ...... F25D 11/025 |
| 2018/0126325 A1 | 5/2018 | Sher |
| 2018/0171603 A1 | 6/2018 | Di Benedetti et al. |
| 2019/0100903 A1 | 4/2019 | Panda et al. |
| 2019/0234053 A1 | 8/2019 | Kim et al. |
| 2020/0108344 A1 | 4/2020 | Vollmer et al. |
| 2021/0254315 A1* | 8/2021 | Garg ...................... C02F 1/003 |

\* cited by examiner

SOLAR POWERED WATER COLLECTION, TREATMENT AND DISPENSER SYSTEM

CROSS-REFERENCE TO RELATED APPLICATIONS

This application claims the benefit of U.S. Provisional Patent Application Ser. No. 63/074,272 filed on Sep. 3, 2020, which is incorporated by reference herein in its entirety.

FIELD OF THE INVENTION

The present invention relates generally to a solar powered water collection, treatment and dispenser system.

BACKGROUND OF THE INVENTION

Most people are taught from a very early age about the importance and life-giving qualities attributed to a simple little molecule upon which nearly each and every living thing on the planet relies upon to survive, namely, water.

As children, we learn that the makeup of the human body is about 70% water. We also learn that the many oceans and seas cover about 70% of the Earth's surface. Of course, we then learn that despite being surrounded by such vast bodies of water. i.e., the water in the oceans and seas accounts for over 95% of the water found on the planet, most of it is not suitable for consumption by humans and many other living organisms due to the large amount of dissolved salts and other components found in seawater.

In fact, the freshwater found in all of the lakes and rivers on the planet, as well as all of the water contained in the surrounding atmosphere, only account for about 1% of the water found on the planet Earth. Another 1.5% or so is found in the groundwater in subterranean aquifers, while the remaining 2% or so of the planets water is found frozen in the polar caps, glaciers and icebergs which break off therefrom and drift out to sea.

To serve the needs of large populations of people such as are found in the cities, towns, and suburbs throughout the world, large municipal water collection and treatment facilities have been built and will continue to be built by governments and/or nongovernment agencies in attempts to meet the water demands of a rapidly increasing world population. These large municipal facilities may divert water from lakes and rivers, drill to access deeply submerged freshwater aquifers, and more recently, attempt to build large-scale energy efficient water desalination facilities in coastal areas.

Unfortunately, despite the abundance of water present in various forms and the large scale municipal water collection and treatment facilities noted above, a combination of human encroachment, deforestation, pollution, and the changing climate, which some still believe to be in question, the United Nations has reported that it is likely that nearly ⅔ of the world's population will face water shortages in one form or another as soon as year 2025, which is just around the corner.

Furthermore, in many parts of the world, ii often is simply not possible to find sufficient water reserves to supply such large-scale municipal water collection and treatment facilities as noted above. In addition, in some instances where sufficient water reserves do exist, the enormous amount of money required to design, build and operate such large municipal facilities simply are not available. And even where such large facilities are constructed and operating, the ability to transmit clean potable water to people living in the outer reaches, beyond the cities, towns, and suburbs, often prevent access to clean potable water to large portions of the population living in more remote locations.

For thousands of years, people located in remote areas have looked to the ground in order to meet their needs for freshwater by drilling shallow wells to tap into shallow underground freshwater aquifers. Unfortunately, however, increased runoff including all forms of pollutants which find their way into shallow underground freshwater aquifers increasingly render these sources of freshwater unsuitable for human consumption. The increasing instances of viruses and other pathogens impacting human health, such as, the most recent novel coronavirus, more commonly known as COVID-19, add yet another layer of concern in producing water suitable for human consumption.

Although freshwater obtained from potentially contaminated shallow underground freshwater aquifers may be treated to remove contaminants and/or kill pathogens in order to make it suitable for human consumption, the treatment equipment necessary to perform such operations and/or the electricity required to operate such treatment equipment are often unavailable in remote areas in which the shortage of water for human consumption is often most critical.

The lack of fresh potable water is also an issue, albeit on a smaller scale, for persons conducting activities in remote locations, such as remote construction sites, remote rescue operations, as well as various research and recreational activities in which people willingly venture into remote areas of the planet for extended periods of time were sources of fresh potable water simply are not readily available.

Accordingly, there is an established need for a solution to one or more of the serious problems related to water collection, treatment and dispensing noted above.

SUMMARY OF THE INVENTION

The present invention is directed to a solar powered water collection, treatment and dispenser system.

In a first implementation of the invention, a solar powered water collection, treatment and dispenser system which condenses water from surrounding moisture laden air, treats the condensed water, and dispenses the treated water to a user may comprise: a housing assembly having a plurality of compartments at least partially enclosed therein; a solar power assembly having at least one solar collection panel mounted to the housing assembly to generate electrical power to operate the system; a collection assembly having an air intake unit mounted through a portion of the housing assembly to draw in the surrounding moisture laden air, wherein the collection assembly further comprises a dehumidifier unit mounted in one of the plurality of compartments of the housing assembly to condense untreated water from the moisture laden air drawn in through the air intake unit; a reverse osmosis assembly mounted in one of said plurality of compartments of the housing assembly and disposed in communication with the collection assembly to remove contaminants from the untreated water to produce treated water; a hot water assembly having a heated water tank mounted in one of the plurality of compartments of the housing assembly which receives treated water from the reverse osmosis assembly and dispenses hot treated water to the user therefrom via a hot water dispenser; and, a cold water assembly having a cooled water tank mounted in one of the plurality of compartments of the housing assembly which receives treated water from the reverse osmosis assembly and dispenses cold treated water to the user therefrom via a cold water dispenser.

In a second aspect, the solar powered water collection, treatment and dispenser system can include a housing assembly having wheels to facilitate staging the system wherever desired.

In another aspect, the solar powered water collection, treatment and dispenser system may have a solar power assembly including an inverter to convert a direct current produced by one or more solar collection panels to an alternating current electrical power supply to operate the system.

In a further aspect, the solar powered water collection, treatment and dispenser system can include a solar power assembly having at least one storage cell to store excess electrical power generated by one more solar collection panels.

In one other aspect, the solar powered water collection, treatment and dispenser system may have an air filter to remove particulate matter present in the surrounding moisture laden air drawn in through an air intake unit.

In still another aspect, the solar powered water collection, treatment and dispenser system can include an air purifier to kill pathogens present in the surrounding moisture laden air drawn in through an air intake unit, wherein the air purifier may comprise an ultraviolet light unit.

In yet one further aspect, the solar powered water collection, treatment and dispenser system may have a collection unit disposed in communication with a dehumidifier unit to receive untreated condensed water therefrom.

In still one other aspect, the solar powered water collection, treatment and dispenser system can include a reverse osmosis assembly having a primary reverse osmosis unit and a secondary reverse osmosis unit arranged in a series configuration, such as in a dual pass reverse osmosis system, or arrange in a parallel configuration to increase throughput through the reverse osmosis assembly.

In yet another aspect, the solar powered water collection, treatment and dispenser system may have a reverse osmosis assembly including a contaminant meter disposed to monitor a level of contaminants remaining in the treated water discharged from a primary reverse osmosis unit and/or a secondary reverse osmosis unit.

In still one further aspect, the solar powered water collection, treatment and dispenser system can include a heater unit and/or a cooling unit to maintain treated water from a reverse osmosis assembly in a heated or cooled water tank at a preselected heated temperature, respectively.

In yet one other aspect, the solar powered water collection, treatment and dispenser system may have a heated water tank gauge and/or a cooled water tank gauge to monitor an amount or volume of treated water from a reverse osmosis assembly contained in a heated water tank or a cooled water tank, respectively.

In even another aspect, the solar powered water collection, treatment and dispenser system may have a recirculation assembly comprising a control valve unit operable to recirculate treated water discharged from a reverse osmosis assembly back to the reverse osmosis assembly if the level of contaminants remaining in the treated water is above a predetermined contaminant limit.

In one further aspect, the solar powered water collection, treatment and dispenser system can include a control assembly having a control panel mounted to said housing assembly and accessible to the user to program select operating parameters for the system.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "top", "bottom", "left", "right", "front", "rear", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed to a solar powered water collection, treatment and dispenser system.

Figure 1:
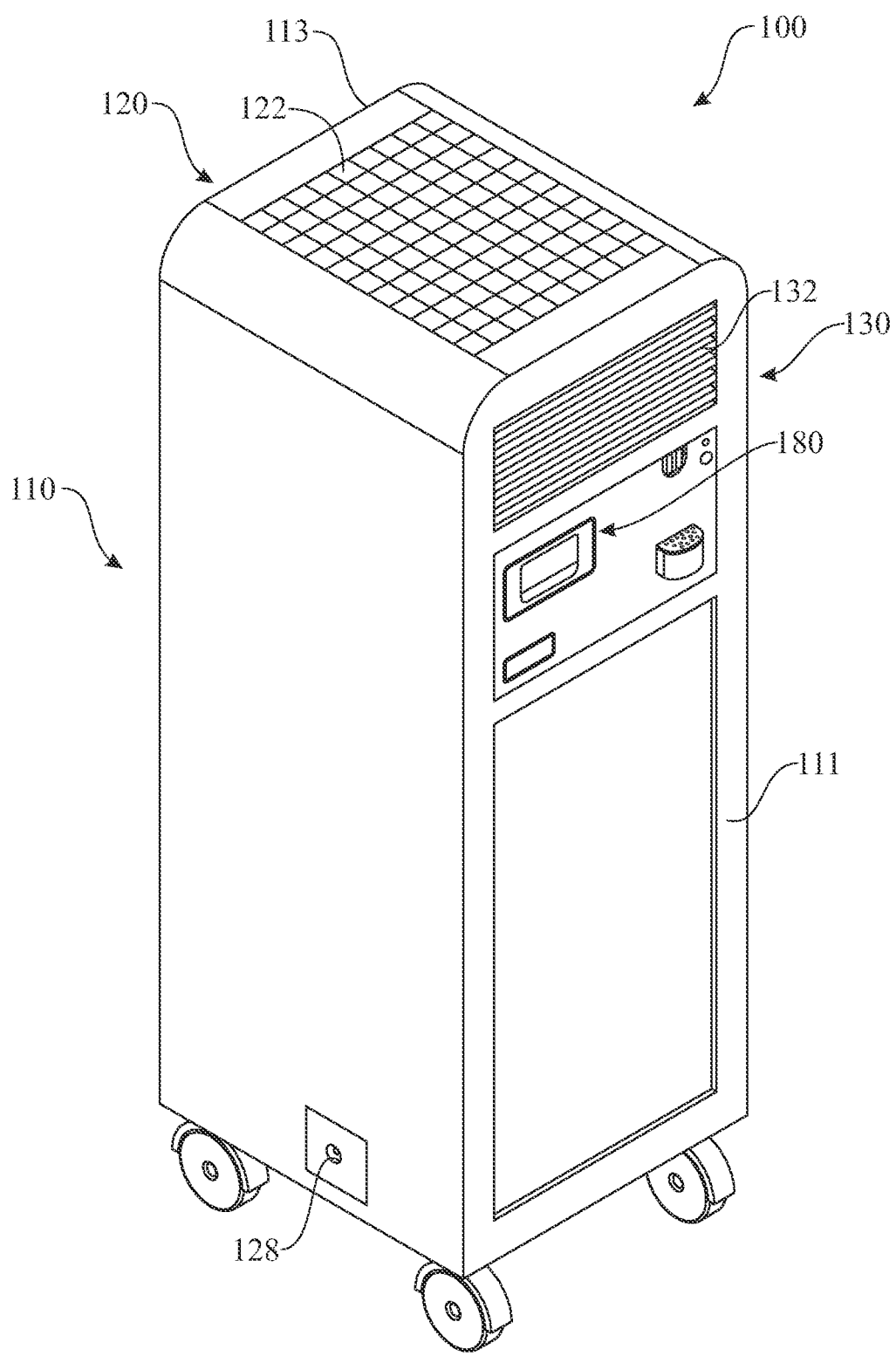
FIG. 1 presents a top front perspective view of one illustrative embodiment of a solar powered water collection, treatment and dispenser system, in accordance with the present invention.
Figure 2:
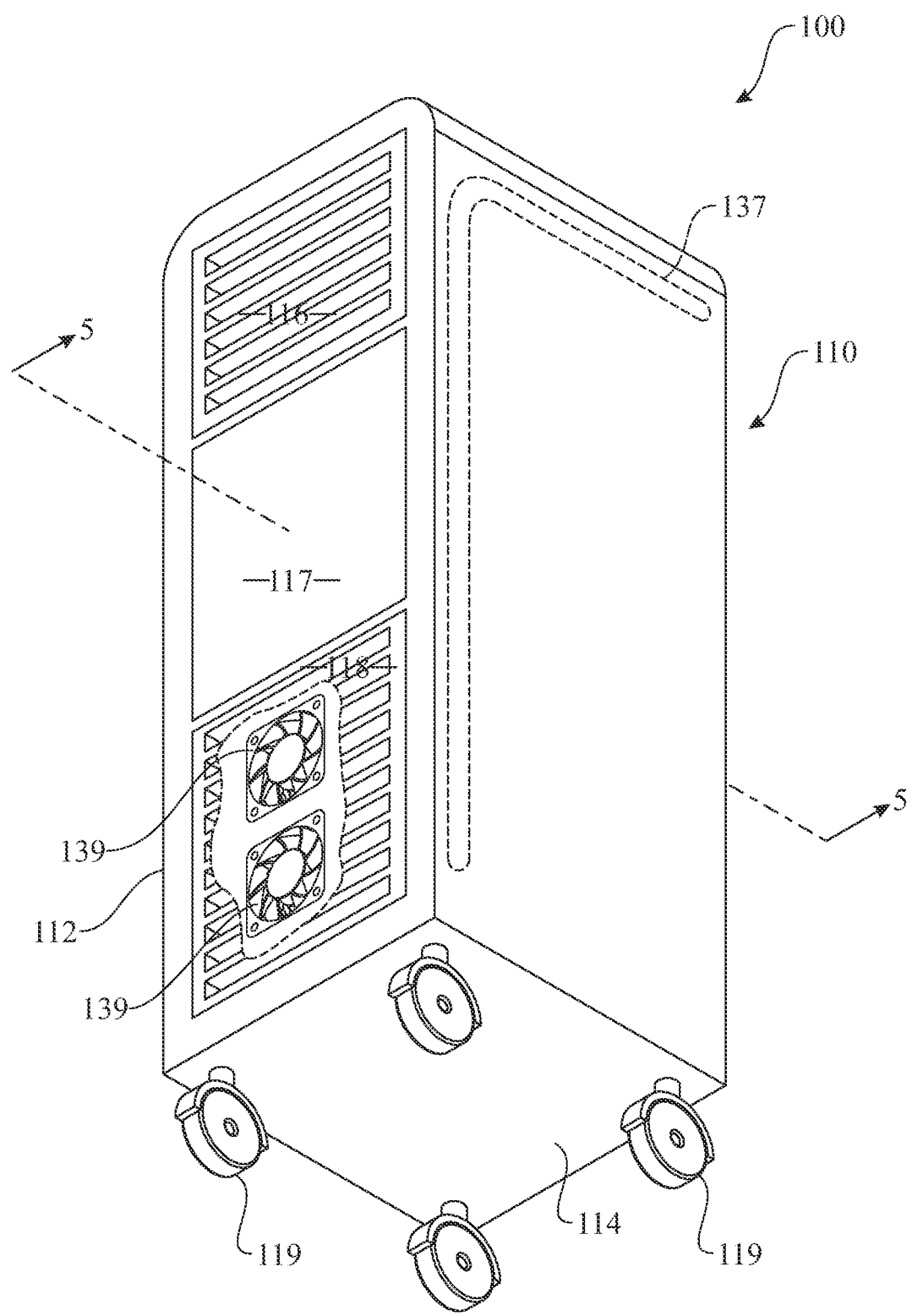
FIG. 2 presents a bottom rear perspective view of the solar powered water collection, treatment and dispenser system of FIG. 1, in accordance with the present invention.

Referring initially to FIGS. 1 and 2, top front and bottom rear perspective views of one illustrative embodiments of a solar powered water collection, treatment and dispenser system, respectively, are presented. As shown throughout the figures, a solar powered water collection, treatment and dispenser system in accordance with the present invention is generally shown as at 100.

Beginning with the illustrative embodiment of FIG. 1, a solar powered water collection, treatment and dispenser system 100 comprises a housing assembly 110 having a front 111 and a top 113. As shown in FIG. 2, a housing assembly 110 includes a rear 112 and a bottom 114. In at least one embodiment, a housing assembly 110 of a solar powered water collection, treatment and dispenser system 100 includes a plurality of compartments at least partially enclosed therein. As shown in the illustrative embodiment of FIG. 2, a housing assembly 110 includes a collection and treatment compartment 116, a hot storage compartment 117, and a cold storage compartment 118. As also shown in FIG. 2, in at least one embodiment, a housing assembly 110 comprises a plurality of casters or wheels 119 mounted to the bottom 114 of the housing assembly 110. As will be appreciated, the plurality of wheels 119 allow the present solar powered water collection, treatment and dispenser system 100 to be easily staged for operation wherever needed.

As the name implies, a solar powered water collection, treatment and dispenser system 100 in accordance with the present invention includes a solar power assembly 120. A solar power assembly 120 is configured to generate at least enough electrical power to operate each of the components of a solar powered water collection, treatment and dispenser system 100, such as are described in greater detail hereinafter. In at least one further embodiment, a solar power assembly 120 is further configured to generate excess electrical power such as may be stored for uninterrupted operation of the present system 100 during periods of low or no light and/or to provide electrical power to ancillary components, such as via a charger port 128 as shown in FIG. 1.

Figure 8:
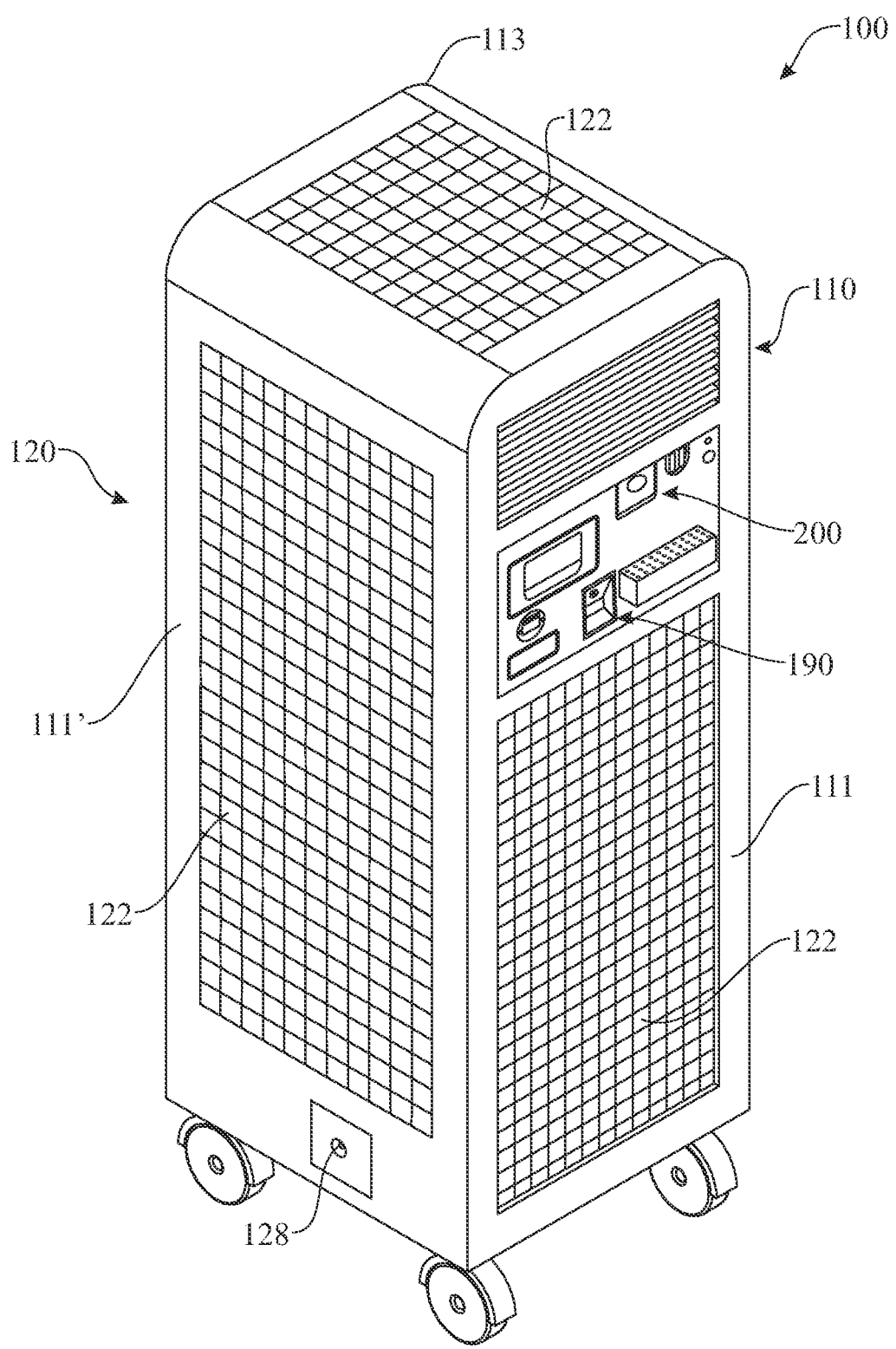
FIG. 8 presents a top front perspective view of another illustrative embodiment of a solar powered water collection, treatment and dispenser system, in accordance with the present invention.
Figure 9:
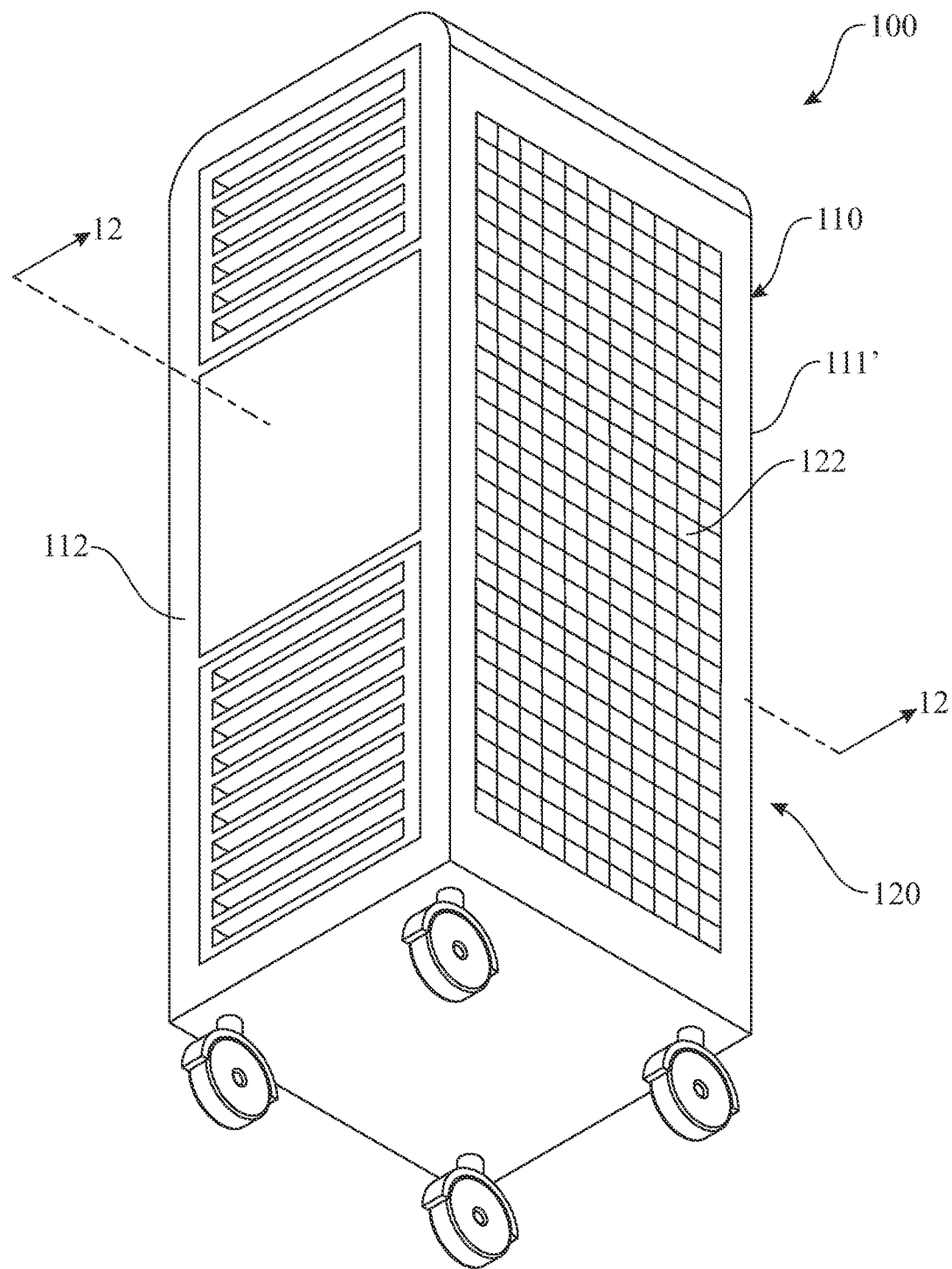
FIG. 9 presents a bottom rear perspective view of the solar powered water collection, treatment and dispenser system of FIG. 8, in accordance with the present invention.

With reference once again to FIG. 1, in at least one embodiment a solar power assembly 120 comprises at least one solar collection panel 122 which, in accordance with the illustrative embodiment of FIG. 1, is mounted to the top 113 of the housing assembly 110. It is to be appreciated that a solar power assembly 120 in accordance with the present invention may comprise a plurality of solar collection panels 122, and further, that the plurality of solar collection panels 122 may be mounted to the top 113 of the housing assembly, such as is shown in FIG. 1, as well as being mounted to the top 113, front 111 and sides 111', such as is shown in the illustrative embodiment of FIG. 8. In at least one further embodiment, one or more solar collection panel 122 is mounted in an elevated and/or outwardly extended orientation from the housing assembly 110. It is further to be appreciated that a solar collection panel 122 of a solar power assembly 120 in accordance with the present invention may comprise any of a number of photovoltaic cells, and may comprise monocrystalline, polycrystalline, thin-film and/or amorphous types of construction, just to name a few.

Figure 5:
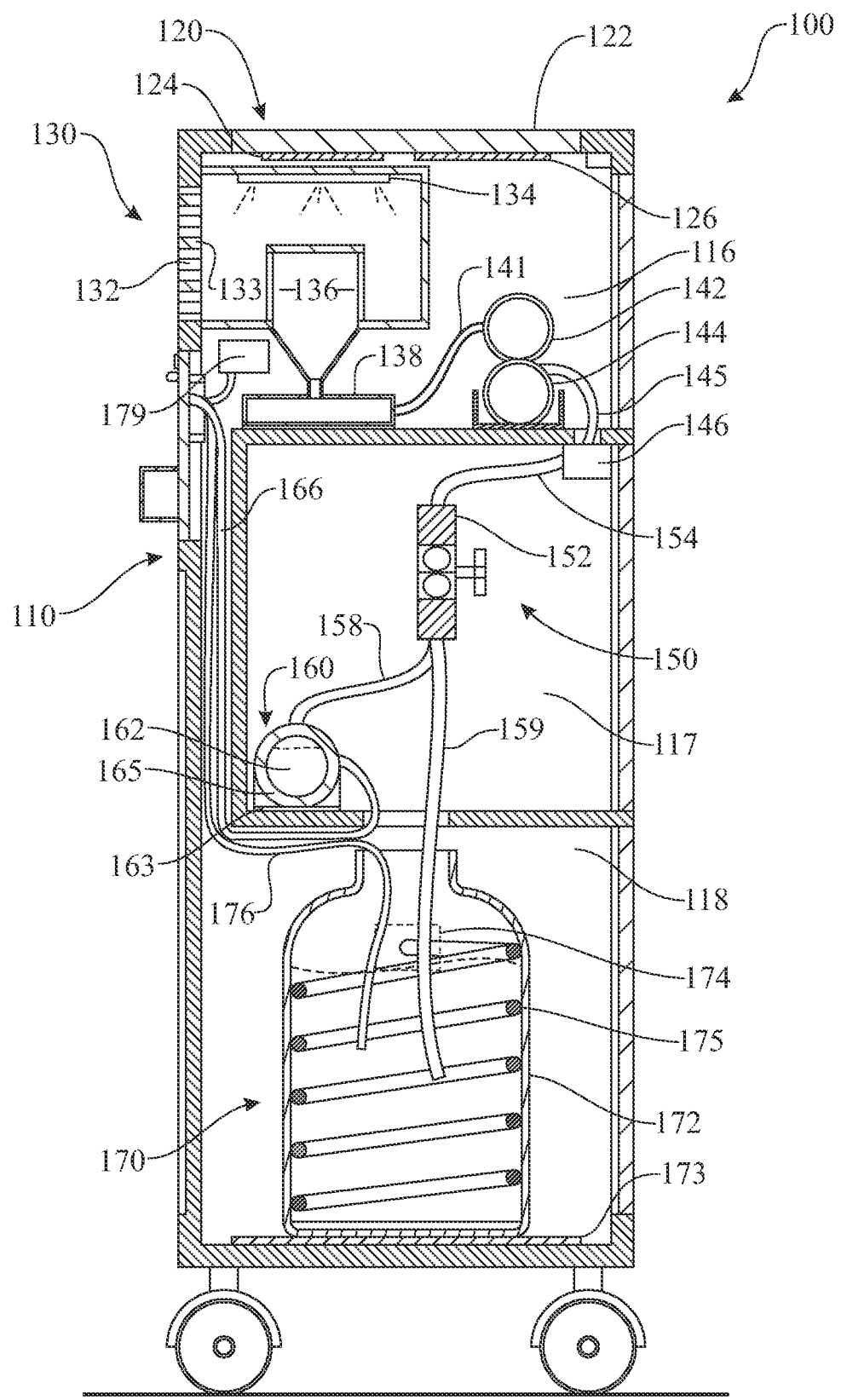
FIG. 5 presents a cross-sectional view of the solar powered water collection, treatment and dispenser system of FIG. 2 along lines 5-5 thereof, in accordance with the present invention.
Figure 12:
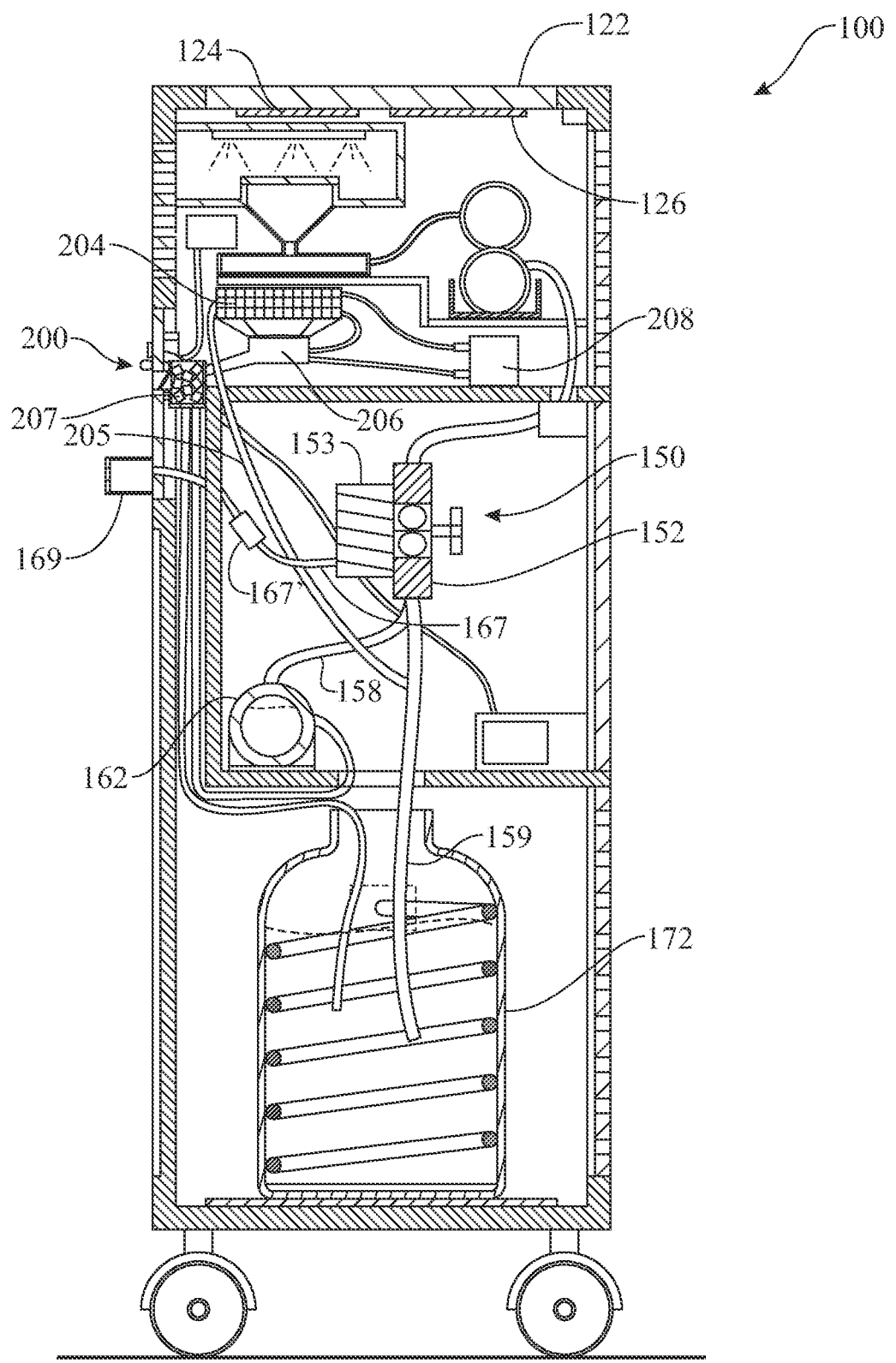
FIG. 12 presents a cross-sectional view of the solar powered water collection, treatment and dispenser system of FIG. 9 along lines 12-12 thereof, in accordance with the present invention.

Looking next to FIGS. 5 and 12, in at least one embodiment, a solar power assembly 120 further comprises an inverter 124 disposed in communication with at least one solar collection panel 122. An inverter 124 is utilized to convert the direct current or DC voltage which is produced by a solar collection panel 122 into an alternating current or AC voltage which may be utilized by the various components of a solar powered water collection, treatment and dispenser system 100 in accordance with at least one embodiment of the present invention.

Also shown in FIGS. 5 and 12, a solar power assembly 120 in accordance with the present invention further comprises a storage cell 126, once again, disposed in communication with the solar collection panel 122. As before, a solar power assembly 120 may be configured to generate at least enough electrical power to operate each of the components of a solar powered water collection, treatment and dispenser system 100, however, in at least some embodiments, a solar power assembly is configured to generate an excess of electrical power. In such an embodiment, a solar power assembly 120 comprises a storage cell 126 in order to store the excess electrical power generated by one or more solar collection panels 122 for use at a later time, such as, when little or no light is available to generate electrical power via one or more solar collection panels 122. Also as before, excess electrical power generated by one or more solar collection panels 122 may be stored in a storage cell 126 for use in providing power to ancillary devices via a charging port 128, such as shown in the illustrative embodiments of FIGS. 1 and 8. It is to be appreciated, the charging port 128 may also be utilized to connect an external electrical power source to the present solar powered water collection, treatment and dispenser system 100 so as to charge a storage cell 126 to allow for operation of the system 100 when sufficient light is simply not available for the solar power assembly 120 to generate enough electrical power to operate the system.

It is to be appreciated that a storage cell 126 in accordance with the present invention may comprise any of a number of rechargeable power sources. In accordance with at least one embodiment of a solar powered water collection, treatment and dispenser system 100, a storage cell 126 comprises one or more lithium ion rechargeable batteries.

A solar powered water collection, treatment and dispenser system 100 in accordance with at least one embodiment of the present invention further comprises a collection assembly 130. In at least one embodiment, a collection assembly 130 includes an air intake unit 132 to draw moisture laden air from the environment surrounding the solar powered water collection, treatment and dispenser system 100 into at least a portion of the housing assembly 110 thereof such as, by way of example, a collection and treatment compartment 116 as described hereinabove. As may be seen from FIG. 1, in at least one embodiment, an air intake unit 132 comprises a grated configuration to facilitate passage of moisture laden air therethrough.

Looking again to FIG. 5, an air intake unit 132 of a collection assembly 130 further comprises an air filter 133 in accordance with at least one embodiment of the present invention. More in particular, in at least one embodiment, an air filter 133 is positioned across the grated portion of the air intake unit 132 so as to capture and remove particulate matter present in the surrounding moisture laden air which is drawn into the collection and treatment compartment 116 by the air intake unit 132. As will be appreciated, an air filter 133 in accordance with the present invention may be selected to capture and remove particulate matter having a specified effective diameter such as, by way of example only, ranging from about 1 micron to about 100 microns.

With continued reference to FIG. 5, a collection assembly 130 in accordance with at least one embodiment of the present invention further comprises an air purifier unit 134. More specifically, an air purifier unit 134 is provided to kill pathogens which may be present in the surrounding moisture laden air which is drawn into the present solar powered water collection, treatment and dispenser system 100 in accordance with the present invention. In at least one embodiment, an air purifier unit 134 comprises an ultraviolet light generation unit such as is known to be effective in killing air and water borne pathogens. As will be appreciated, an air intake unit 132 which combines an air filter 133 and an air purifier unit 134 will result in moisture laden air which is substantially free of particulate matter and/or potentially harmful pathogens.

Figure 10:
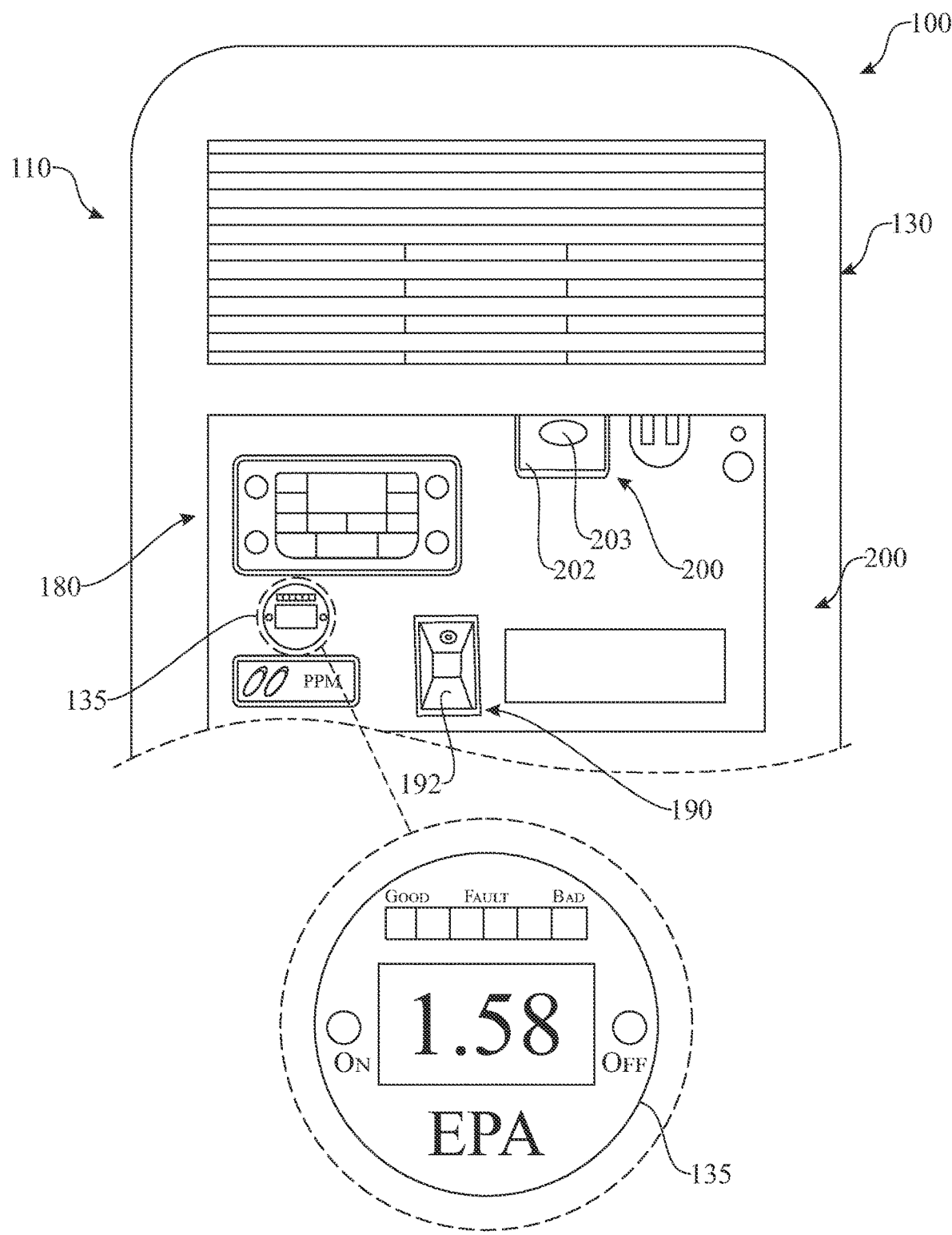
FIG. 10 presents a front elevation of an upper portion of the solar powered water collection, treatment and dispenser system of FIG. 8, in accordance with the present invention.

In at least one embodiment, a collection assembly 130 in accordance with the present invention includes a digital air quality meter 135, such as is shown best by way of example in FIG. 10. A digital air quality meter 135 is provided to measure and indicate the quality of the ambient air surrounding the intake of the present solar powered water collection, treatment and dispenser system 100, and to at least partially control the operation thereof. More in particular, a digital air quality meter 135 in at least one embodiment is disposed in communication with a control assembly 180, as discussed hereinafter, such that the control assembly 180 can modify the operational parameters of an air purifier unit 134 based on the measured quality of incoming air through the air intake unit 132 by the digital air quality meter 135.

A collection assembly 130 in at least one embodiment of the present invention further comprises a dehumidifier unit 136 which condenses untreated water from the moisture laden air which is drawn into a solar powered water collection, treatment and dispenser system 100 in accordance with the present invention. In at least one further embodiment of the present invention, a collection assembly 130 comprises a plurality of dehumidifier units 136, for example, a double dehumidifier unit 136, in order to condense water from the moisture laden air which is drawn into a solar powered water collection, treatment and dispenser system 100 by an air intake unit 132, such as described above. Looking once again to FIG. 5, a collection assembly 130 in accordance with the present invention comprises a dehumidifier unit 136 which receives surrounding moisture laden air which is drawn in via air intake unit 132 through air filter 133 and exposed to air purifier 134, prior to entry to dehumidifier unit 136. As also shown in FIG. 5, the collection assembly 130 further comprises a collection unit 138 which receives and at least temporarily stores untreated water condensed out from the surrounding moisture laden air by a dehumidifier unit 136, prior to further treatment in the present solar powered water collection, treatment and dispenser system 100 in accordance with the present invention.

Looking next to FIG. 2, in at least one embodiment, a collection assembly 130 includes an exhaust duct 137 to dissipate heat generated by operation of dehumidifier unit(s) 136 out of the housing assembly 110. At least one exhaust blower 139 may be disposed in communication with the exhaust duct 137 to facilitate the capture and diversion the heat generated by the dehumidifier unit(s) 136 out of the housing assembly 110. With reference once again to FIG. 2, in at least one embodiment, a collection assembly 130 comprises a plurality of exhaust blowers 139 to facilitate the capture and diversion the heat generated by the dehumidifier unit(s) 136 out of the housing assembly 110.

A solar powered water condenser, treatment and dispenser system 100 further comprises a reverse osmosis assembly 140 in accordance with at least one embodiment of the present invention. A reverse osmosis assembly 140 receives and processes untreated water condensed from the surrounding moisture laden air by a collection assembly 130. More in particular, a reverse osmosis assembly 140 removes contaminants from the untreated water by forcing water molecules under pressure through a semipermeable membrane. During the process, contaminants are filtered out to produce treated, potable drinking water.

A reverse osmosis assembly 140 in one embodiment comprises a primary reverse osmosis unit 142 and a secondary reverse osmosis unit 144. As may be seen from FIGS. 4 and 5, a primary reverse osmosis unit 142 and a secondary reverse osmosis unit 144 are disposed in a series configuration, sometimes referred to as a dual pass reverse osmosis system. As will be appreciated, a primary reverse osmosis unit 142 and a second reverse osmosis unit 144 may be operated in parallel so as to increase the throughput of untreated water processed by a reverse osmosis assembly 140 in accordance with the present invention. With particular reference to FIG. 5, the reverse osmosis assembly 140 includes an untreated water inlet 141 which transfers untreated water condensed out from the surrounding moisture laden air from a collection unit 138 of the collection assembly 130 to a primary reverse osmosis unit 142. As will be appreciated, a pump, not shown for clarity, may be utilized to transfer the untreated water from the collection unit 138 to the primary reverse osmosis unit 142.

Figure 3:
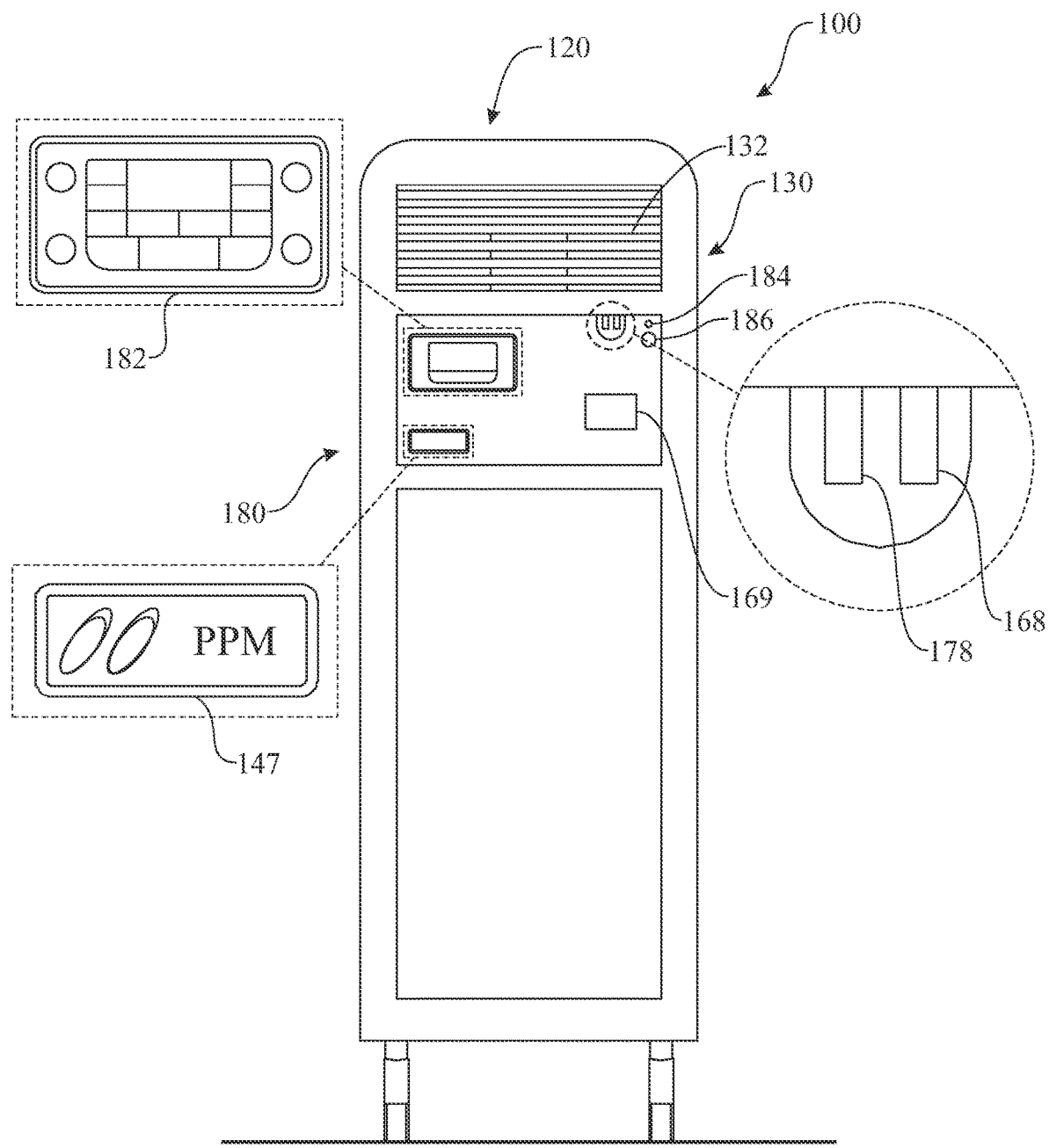
FIG. 3 presents a front elevation of the solar powered water collection, treatment and dispenser system of FIG. 1, in accordance with the present invention.
Figure 4:
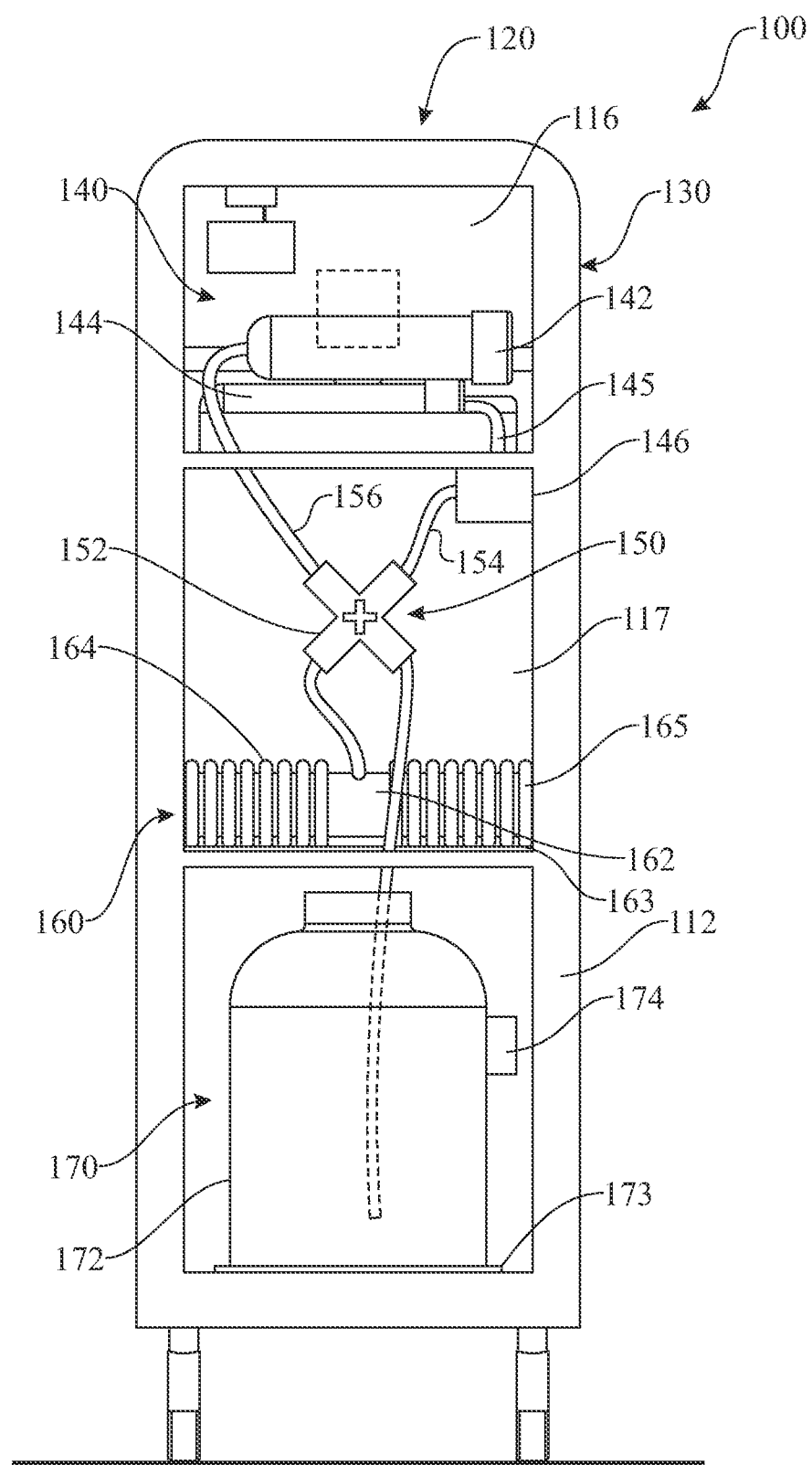
FIG. 4 presents a rear elevation of the solar powered water collection, treatment and dispenser system of FIG. 1 having back panels removed to show the internal components thereof, in accordance with the present invention.

As shown in FIGS. 4 and 5, a reverse osmosis assembly 140 further comprises a treated water outlet 145 which receives treated water after it has passed through both the primary reverse osmosis unit 142 and the secondary reverse osmosis unit 144. As further shown in FIGS. 4 and 5, the treated water which is passed through the primary reverse osmosis unit 142 and the secondary reverse osmosis unit 144 is directed to a contaminant meter 146 via treated water outlet 145. More in particular, a contaminant meter 146 is provided to monitor the level of contaminants remaining in the treated water discharged from the reverse osmosis units 142, 144, in order to assure proper operation of the reverse osmosis units 142, 144. In at least one embodiment of a solar powered water collection, treatment and dispenser system 100, a reverse osmosis assembly 140 further comprises a contaminant meter display 147, such as is shown by way of example in the illustrative embodiment of FIG. 3, to provide a visual indication as to whether the concentration of contaminants remaining in the treated water discharged from the reverse osmosis units 142, 144, such as may be measured and pails-per-million (PPM), is within acceptable predetermined treatment limits. As will be appreciated, a visual contaminant meter display 147 can serve to alert an operator of a solar powered water collection, treatment and dispenser system 100 in accordance with the present invention of the need to service the reverse osmosis assembly 140 therein.

In one embodiment, a solar powered water collection, treatment and dispenser system 100 further comprises a recirculation assembly 150 utilized to recirculate treated water discharged from a reverse osmosis assembly 140 in the event the concentration of contaminants remaining in the treated water discharged from reverse osmosis units 142, 144 exceeds acceptable predetermined limits. A recirculation assembly 150 in accordance with at least one embodiment of the present invention comprises a control valve unit 152 which is operable with a control assembly 180, discussed in greater detail below, to direct treated water either one of a plurality of storage/dispenser containers or back to a reverse osmosis assembly 140 for further treatment, as may be required. With reference once again to FIGS. 4 and 5, a control valve unit 152 in at least one embodiment comprises an X or cross-valve having a treated water inlet 154 and a plurality of water outlets. Looking specifically to FIG. 4, the control valve unit 152 includes a recirculated water outlet 156 which is directed to the inlet of a primary reverse osmosis unit 142 of the reverse osmosis assembly 140. With continued reference to FIG. 4, the control valve unit 152 further includes a primary treated water outlet 158, which discharges treated water from the reverse osmosis assembly 140 to a heated water tank 162 of a hot water assembly 160 as described in greater detail hereinafter. Also shown in the illustrative embodiment of FIG. 4, the control valve unit 152 further comprises a secondary treated water outlet 159 which discharges treated water from the reverse osmosis assembly 140 to a cooled water tank 172 of a cold water assembly 170, also described in greater detail hereinafter.

Looking next to FIG. 12, a recirculation assembly 150 in accordance with at least one embodiment of the present invention further comprises a digital pump 153 operative with the control valve unit 152. As will be appreciated, the digital pump 153 may be actuated as needed to pump water through the control valve unit 152 to the recirculated water outlet 156 and into the inlet of a primary reverse osmosis unit 142 of the reverse osmosis assembly 140 for further treatment, such as may be necessitated upon receipt of an indication that the concentration of contaminants remaining in the treated water discharged from the reverse osmosis units 142, 144 is outside of acceptable predetermined treatment limits. Alternatively, the digital pump 153 may be actuated to pump treated water through the primary treated water outlet 158 into the heated water tank 162 and/or through the secondary treated water outlet 159 into the cooled water tank 172. As will further be appreciated, the digital pump 153 may also be utilized to transfer an amount of treated water from the heated water tank 162 to the cooled water tank 172, or vise versa, by selective operation of the control valve unit 152.

As will be appreciated, a recirculation assembly 150 having a combination of a control valve unit 152 comprising an X or cross-valve configuration and a digital pump 153 provides ultimate control over the disposition of treated water from a reverse osmosis assembly 140 in accordance with the present invention. As one example, as before, in the event a monitored contaminant level in the treated water is above an acceptable predetermined treatment limit, the treated water is simply recirculated back to the reverse osmosis assembly 140 through the control valve unit 152 by the digital pump 153 until such time as acceptable contaminant concentration levels have been obtained. As another example, depending on a volume of treated water contained in either a heated water tank 162 or a cooled water tank 172, the digital pump 153 may direct treated water through the control valve unit 152 into either or both, as warranted.

Figure 6:
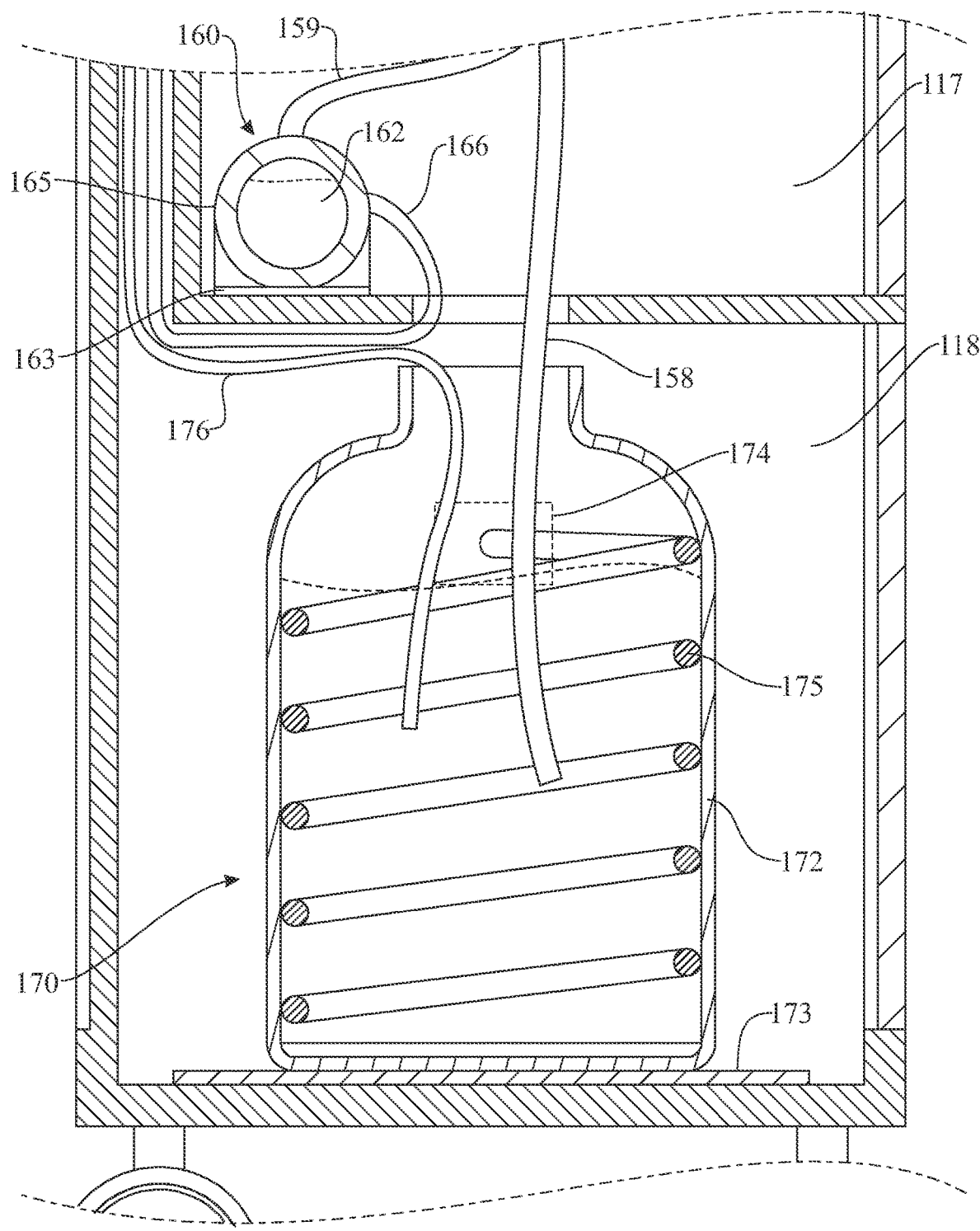
FIG. 6 presents an enlarged cross-sectional view of a lower portion of the solar powered water collection, treatment and dispenser system of FIG. 5, in accordance with the present invention.

As mentioned above, in at least one embodiment, a solar powered water collection, treatment and dispenser system 100 in accordance with the present invention further comprises a hot water assembly 160. With reference to FIGS. 4 through 6, a hot water assembly 160 includes a heated water tank 162. A heated water tank 162 in accordance with the present invention is constructed of a durable, non-toxic, and sterile material of construction such as is acceptable for storage and/or dispensing of potable water. In at least one embodiment, a heated water tank 162 is constructed of aluminum. As will be further appreciated, a heated water tank 162 may comprise any of a number of internal volumes depending on the ultimate capacity requirements of a solar powered water collection, treatments and dispenser system 100 in accordance with the present invention. As just one example, a heated water tank 162 may have a capacity of 1 pint, 1 quart, 1 gallon, or even 10 gallons or 100 gallons. In at least one embodiment of the present invention, the heated water tank 162 comprises a capacity of about 3 quarts.

A hot water assembly 160 in accordance with the present invention includes a heated water tank gauge 163 which monitors an amount or volume of treated water contained within the heated water tank 162. A heated water tank gauge 163 may comprise any of a number of devices utilized to measure an amount or volume of material in a tank, such as, a visual sensor, a float switch, or a scale to measure the mass of treated water contained within the heated water tank 162. As will be appreciated, a heated water tank gauge 163 in communication with a control assembly 180 may be utilized to operate a control valve unit 152 in order to initiate or terminate a discharge of treated water to the heated water tank 162, based on a preselected volume limit therein.

A hot water assembly 160 further comprises a heating unit 164 so as to maintain a volume of treated water within the heated water tank 162 at a preselected heated water temperature. In at least one embodiment, a preselected heated water temperature is about 120 degrees Fahrenheit. As may be seen from FIGS. 4 and 5, a heating unit 164 in accordance with at least one embodiment of the present invention comprises a plurality of heating coils 165 disposed in an at least partially surrounding relation to the heated water tank 162. With further reference to FIG. 5, a hot water assembly 160 also includes a hot water discharge line 166 which transfers hot treated water from the heated water tank 162 to a hot water dispenser 168, such as is shown by way of example in the illustrative embodiment of FIG. 3, where hot treated water is readily accessible to users of the present system 100. A pump or similar mechanism, such as, by way of example, digital pump 153, may be utilized to transfer hot treated water from the heated water tank 162 to the hot water dispenser 168 in accordance with at least one embodiment of the present invention.

As also shown in FIG. 3, at least one embodiment a solar powered water collection, treatment and discharge system 100 further comprises a water collection receptacle 169 to collect any spillage or overspray of treated water while dispensing hot or cold treated water from the present system 100. As will be appreciated, water collected in a water collection receptacle 169 may be routed back to either a collection unit 138 for reprocessing, a heated water tank 162 or a cooled water tank 172, or it may be diverted to an external water drainage system. With reference again to FIG. 12, in at least one embodiment, an overflow return line 167 is provided to transfer water collected in a water collection receptacle 169 to the digital pump 153 such that, once again, it may be routed back to either the reverse osmosis assembly 140 for reprocessing, or to a heated water tank 162 or a cooled water tank 172, or it may be diverted to an external water drainage system. As further shown in FIG. 12, an inline return line filter 167' is provided in at least one embodiment to preliminarily filter water collected in a water collection receptacle 169 prior to reintroduction to the present system 100.

As also mentioned above, at least one embodiment of a solar powered water collection, treatment and dispenser system 100 in accordance with the present invention further comprises a cold water assembly 170. With reference again to FIGS. 4 through 6, a cold water assembly 170 includes a cooled water tank 172. A cooled water tank 172 in accordance with the present invention is again constructed of a durable, non-toxic and sterile material of construction such as is acceptable for storage and/or dispensing of potable water. As with heated water tank 162, in at least one embodiment, a cooled water tank 172 is constructed of aluminum. As will be appreciated, and also as before, a cooled water tank 172 may comprise any number of internal volumes depending on the ultimate capacity requirements of a solar powered water collection, treatments and dispenser system 100 in accordance with the present invention. As just one example, a cooled water tank 162 may have a capacity of 1 quart, 1 gallon, 5 gallons, or even 10 gallons or 100 gallons. In at least one embodiment of the present invention, a cooled water tank 172 comprises a capacity of about 5 gallons.

A cold water assembly 170 in accordance with the present invention includes a cooled water tank gauge 173 which monitors an amount or volume of treated water contained within the cooled water tank 172. As before, a cooled water tank gauge 173 may comprise any of a number of devices utilized to measure an amount or volume of material in a tank, such as, a visual sensor, a float switch, or a scale to measure the mass of treated water contained within the cooled water tank 172. As will be appreciated, a cooled water tank gauge 173 in communication with a control assembly 180 may be utilized to operate a control valve unit 152 in order to initiate or terminate a discharge of treated water to the cooled water tank 172 based on a preselected volume limit therein.

A cold water assembly 170 further comprises a cooling unit 174, such as a compressor, so as to maintain a volume of treated water within the cooled water tank 172 at a preselected cooled water temperature. As may be seen from FIG. 5, a cooling unit 174 in accordance with at least one embodiment of the present invention comprises a plurality of cooling coils 175 disposed within the cooled water tank 172. With further reference to FIG. 5, a cold water assembly 170 also includes a cold water discharge line 176 which transfers cold treated water from the cooled water tank 172 to a cold water dispenser 178, such as is shown, once again, by way of example in the illustrative embodiment of FIG. 3, where cold treated water is readily accessible to users of the present system 100. A pump or similar mechanism, such as, once again, by way of example, digital pump 153 may be utilized to transfer cold treated water from the cooled water tank 172 to the cold water dispenser 178 in accordance with at least one embodiment of the present invention.

As also shown in FIG. 5, at least one embodiment a solar powered water collection, treatment and discharge system 100 further comprises an enhancement unit 179. An enhancement unit 179 is utilized to impart one or more enhancing quality to the hot or cold treated water discharged to a user from the present solar powered water collection, treatment and dispenser system 100. As just one example, an enhancement unit 179 may be utilized to inject an amount of carbon dioxide gas into an amount of hot or cold treated water so as to provide carbonated treated water to a user. As another example, an enhancement unit 179 may be utilized to inject an amount of syrup or powder flavoring into an amount of hot or cold treated water, so as to provide a flavored treated water to a user.

As previously indicated, at least one embodiment the solar powered water collection, treatment and dispenser system 100 in accordance with the present invention comprises a control assembly 180. With reference once again to FIG. 3, a control assembly 180 in one embodiment includes a control panel 182 mounted to a housing assembly 110 so as to be accessible for use and operation by an operator of the present system 100. In one embodiment, the control panel 182 comprises a diagnostic button which will allow a system operator to run a complete check of the present system 100 so as to alert the operator of any operational problem or potential operational problem therein.

Further, and as noted above, the control assembly 180 in accordance with the present invention is operative with a recirculation assembly 150, and more in particular, a control valve unit 152 and/or a digital pump 153 thereof, so as to control the flow of treated water through the present system 100 based upon such factors as contaminant concentration in the treated water, as measured by contaminant meter 146, and/or an amount or volume of treated water in a heated water tank 162 or a cooled water tank 172, as measured by a heated water tank gauge 163 or a cooled water tank gauge 173 respectively, as discussed hereinabove. Further, in the event each of the heated water tank 162 and a cooled water tank 172 are at capacity, the control assembly 180 is operative to discontinue operation of a collection assembly 130 until such time as further treated water is required to be produced to replenish either or both a heated water tank 162 and/or a cooled water tank 172. The control assembly 180 is also operative to bring a storage cell 126 online in the event a solar collection panel 122 is unable to produce sufficient electrical power to operate the present solar powered water collection, treatment and dispenser system 100, such as may occur in low or no light conditions.

With reference once again to FIG. 3, in at least one embodiment, a control assembly 180 further comprises a motion sensor 184 disposed on a housing assembly 110 such that it may detect the presence of a user in a predetermined proximity to the present solar powered water collection, treatment and dispenser system 100. As further shown in FIG. 3, the control assembly 180 also includes a visual indicator 186 such as a light or flashing light source so as to alert a user approaching the present system 100. In at least one embodiment, a visual indicator 186 may be utilized to illuminate a name, logo or emblem associated with the present solar powered water collection, treatment and dispenser system 100. In yet one further embodiment, a control assembly 180 includes a wireless interface 188, including, by way of example only, a Wi-Fi or BLUETOOTH® connection, such as is shown in FIG. 5, so as to allow an operator to remotely access the control assembly 180 as may be required for periodic maintenance and/or servicing.

Turning next to FIGS. 8 through 12, in at least one embodiment, a solar powered water collection, treatment and dispenser system 100 in accordance with the present invention further comprises a vacuum sealing assembly 190. More in particular, a vacuum sealing assembly 190 is operative with a cup or bottle having a sealable straw or tube extending therefrom to evacuate air from the headspace of the cup or bottle, and to crimp and seal the tube or straw until such time as a user elects to consume the contents.

A vacuum sealing assembly 190 includes a sealing receptacle 192 dimensioned and configured to receive a portion of a cup or bottle having the straw or tube therein. A sealing aperture 194 is provided in the sealing receptacle 192, as shown best in FIG. 10, and is dimensioned and configured to receive at least a portion of the sealable tube or straw therein. Once the portion of the sealable tube or straw is inserted into the sealing aperture 194, a vacuum pump 198 is actuated, and air is evacuated from the headspace of the cup or bottle through vacuum line 196 interconnected between the sealing aperture 194 and the vacuum pump 198. As will be appreciated, the vacuum pump 198 is calibrated to produce a minimal vacuum in the headspace of the cup or bottle sufficient to evacuate air therefrom, but not a strong enough vacuum to draw liquid up into and through the vacuum line 196. Once air has been evacuated from the headspace of the cup or bottle, a crimper (not shown) compresses opposite sides of the sealable tube or straw into one another thereby temporarily sealing the contents of the cup or bottle from exposure to the ambient air, as well as to prevent spillage and/or contamination, until such time as a user breaks the seal and consumes the contents therein. As will be appreciated, a sealing assembly 190 is particularly useful when carbonation is added to water dispensed from the present solar powered water collection, treatment and dispenser system 100, so as to retain the carbonation until such time as the beverage is consumed.

With continued reference to FIGS. 8 through 12, a solar powered water collection, treatment and dispenser system 100 in accordance with at least one further embodiment of the present invention also includes an automatic ice dispenser assembly 200. More in particular, an automatic ice dispenser assembly 200 in accordance with at least one embodiment utilizes a portion of the treated water generated by the present system 100 to form ice cubes and at least temporarily store them until such time as a user actuates an ice dispenser 202 to dispense a number of the ice cubes therefrom into a bottle or cup.

Figure 11:
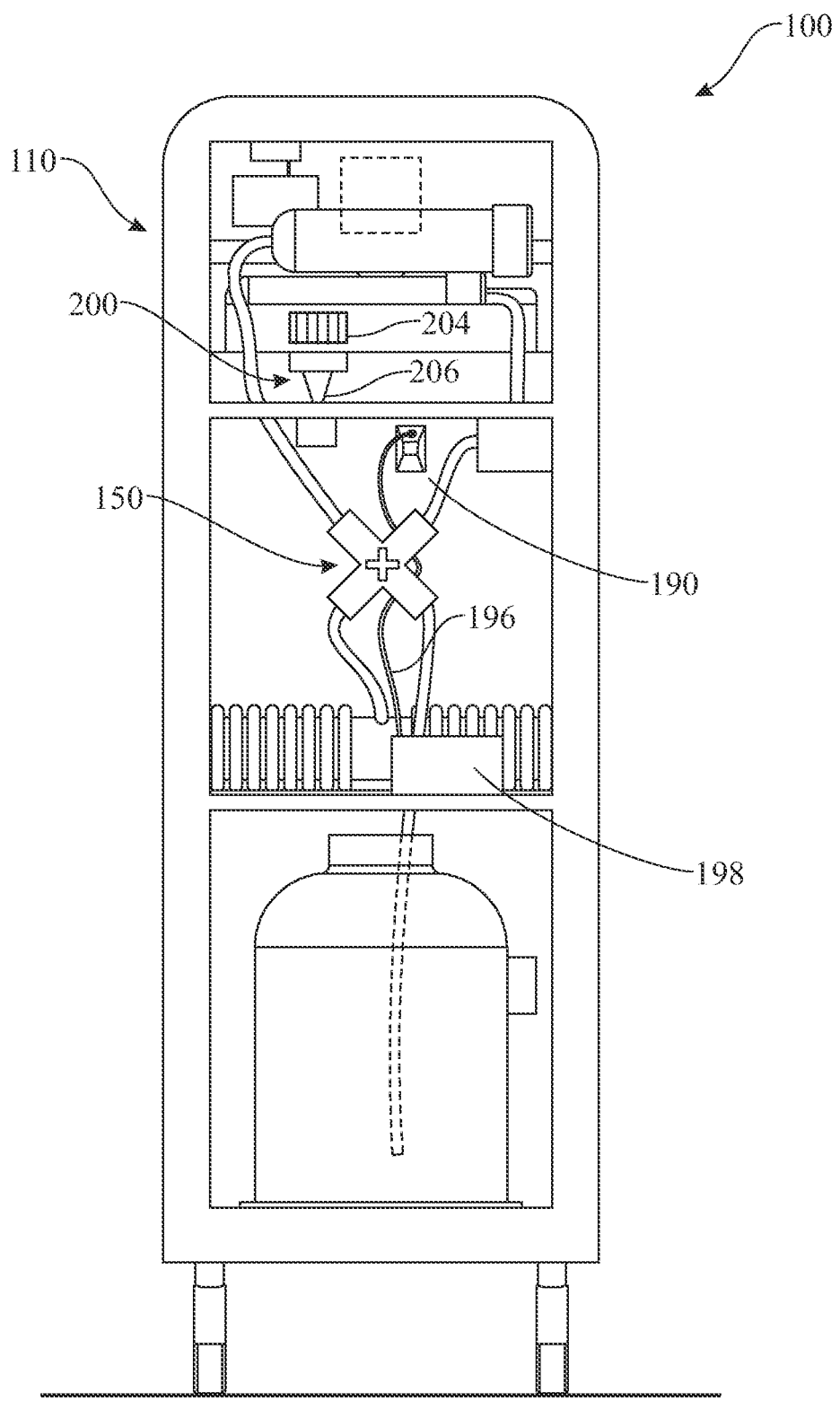
FIG. 11 presents a rear elevation of the solar powered water collection, treatment and dispenser system of FIG. 8 having back panels removed to show the internal components thereof, in accordance with the present invention.

Looking first at FIGS. 11 and 12, an automatic ice dispensing assembly 200 in accordance with the present invention includes an ice tray 204 into which an amount of treated water is added to from ice cubes therefrom. A chiller unit 208 is provided to reduce the temperature of the ice tray 204, and the treated water added thereto via water supply line 205, to a temperature below freezing so as to from the ice cubes in the ice tray 204. Once formed, the ice cubes are released from the ice tray 204 into and through discharge chute 206 and into a storage chamber 207, such as is shown best in FIG. 12, where the ice cubes remain until such time as a user actuates the ice dispenser 202 of the present automatic ice dispensing assembly 200, thereby discharging ice cubes from the storage chamber 207 through the ice dispensing aperture 203 into a bottle, cup or other such receptacle. As will be appreciated, the ice dispenser 202 may be actuated via a mechanical button or lever or by a remote sensor, such as are known in the art. As will be further appreciated, one or more components of the present automatic ice dispenser assembly 200 may be insulated to allow the formation of ice cubes therein, as well as to maintain the ice cubes in a frozen state until dispensed therefrom.

Figure 7:
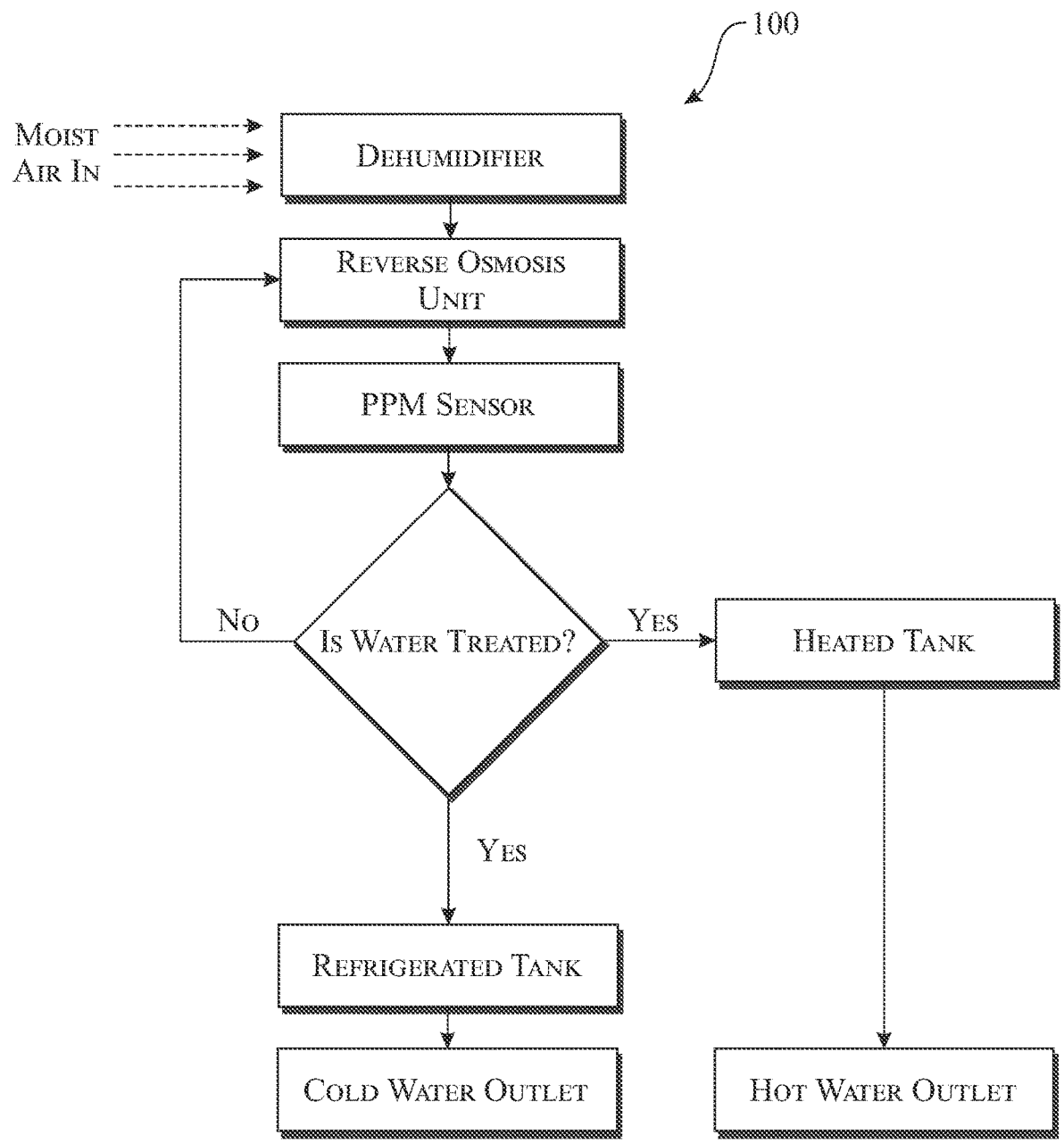
FIG. 7 presents a block diagram of a water flow path through one illustrative embodiment of a solar powered water production and dispenser system in accordance with the present invention.

Having now described the various components comprising the solar powered water collection, treatment and dispenser system 100 in accordance with the present invention,

FIG. 7 presents a block diagram of a water flow path through one illustrative embodiment thereof. As shown in FIG. 7, the process begins with moisture laden air entering the present system 100, such as via a collection assembly 130 as described hereinabove, and the moisture laden air is directed into a dehumidifier, such as dehumidifier unit 136, which condenses untreated water from the moisture laden air. The untreated water is processed via one or more reverse osmosis units, such as primary and secondary reverse osmosis units 142, 144 described above, so as to remove contaminants and to discharge treated water therefrom. As further shown in FIG. 7, the treated water is tested via a contaminant meter, such as a contaminant meter 146 disclosed above, to assure that the level of contaminants in the treated water discharged from the reverse osmosis unit(s) is below acceptable predetermined limits. Upon confirmation that the contaminant level in the treated water is below the acceptable predetermined limits, the treated water is routed to a heated water tank and/or a cool water tank once again, such as disclosed above, and subsequently to a user via a corresponding hot water dispenser or cold water dispenser, once again, such as is disclosed above. As further shown, however, in FIG. 7, in the event that the contaminant level in the treated water is above the acceptable predetermined limits, the treated water is recycled back through reverse osmosis unit(s) until such time as the treated water being discharged from the reverse osmosis unit(s) is below acceptable predetermined limits.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A solar powered water collection, treatment and dispenser system comprising:
    a housing assembly having a front, back, top and bottom, and a plurality of compartments at least partially enclosed therein;
    a solar power assembly having at least one solar collection panel mounted to said top of said housing assembly to generate electrical power to operate said system;
    a collection assembly having an air intake unit mounted through a portion of said housing assembly to draw in the surrounding moisture laden air;
    said collection assembly further comprising a dehumidifier unit mounted in one of said plurality of compartments of said housing assembly to condense untreated water from the moisture laden air drawn in through said air intake unit;
    a reverse osmosis assembly mounted in one of said plurality of compartments of said housing assembly and disposed in communication with said collection assembly to remove contaminants from the untreated water condensed by said dehumidifier unit to produce treated water, said reverse osmosis assembly having a primary reverse osmosis unit and a secondary reverse osmosis unit arranged in a series configuration;
    said reverse osmosis assembly further comprising a contaminant meter disposed to monitor a level of contaminants remaining in the treated water discharged from
said primary reverse osmosis unit and/or said secondary reverse osmosis unit;
a recirculation assembly comprising a control valve unit operable to recirculate the treated water discharged from said reverse osmosis assembly back to said primary reverse osmosis unit if the level of contaminants remaining in the treated water is above a predetermined contaminant limit;
a hot water assembly having a heated water tank mounted in one of said plurality of compartments of said housing assembly which receives treated water from said reverse osmosis assembly and dispenses hot treated water to the user therefrom via a hot water dispenser; and
a cold water assembly having a cooled water tank mounted in one of said plurality of compartments of said housing assembly which receives treated water from said reverse osmosis assembly and dispenses cold treated water to the user therefrom via a cold water dispenser;
wherein said control valve unit is further operable to discharge treated water from said reverse osmosis assembly to said heated water tank; and
wherein said hot water assembly comprises a heated water tank gauge to monitor a volume of treated water in said heated water tank, said heated water tank gauge communicative with said control valve unit to discontinue discharge of treated water from said reverse osmosis assembly to said heated water tank when a predetermined volume of treated water is detected in said heated water tank.

2. The system as recited in claim 1 wherein said housing assembly comprises a plurality of wheels to facilitate staging said system.

3. The system as recited in claim 1 wherein said solar power assembly comprises an inverter to convert a direct current produced by said solar collection panel to an alternating current electrical power supply to operate said system.

4. The system as recited in claim 1 wherein said solar power assembly comprises at least one storage cell to store excess electrical power generated by said at least one solar collection panel.

5. The system as recited in claim 1 wherein said air intake unit comprises an air filter to remove particulate matter present in the surrounding moisture laden air drawn in through said air intake unit.

6. The system as recited in claim 1 wherein said air intake unit comprises an air purifier to kill pathogens present in the surrounding moisture laden air drawn in through said air intake unit.

7. The system as recited in claim 6 wherein said air purifier comprises an ultraviolet light unit.

8. The system as recited in claim 1 wherein said collection assembly further comprises a collection unit disposed in communication with said dehumidifier unit to receive the untreated condensed water therefrom.

9. The system as recited in claim 1 wherein said reverse osmosis assembly further comprises a contaminant meter disposed to monitor a level of contaminants remaining in the treated water discharged from said primary reverse osmosis unit and/or said secondary reverse osmosis unit.

10. The system as recited in claim 1 wherein said hot water assembly comprises a heater unit to maintain treated water from said reverse osmosis assembly in said heated water tank at a preselected heated temperature.

11. The system as recited in claim 1 wherein said hot water assembly comprises a heated water tank gauge to monitor a volume of treated water from said reverse osmosis assembly contained in said heated water tank.

12. The system as recited in claim 1 wherein said cold water assembly comprises a cooling unit to maintain treated water from said reverse osmosis assembly in said cooled water tank at a preselected chilled temperature.

13. The system as recited in claim 1 wherein said cold water assembly comprises a cooled water tank gauge to monitor a volume of treated water from said reverse osmosis assembly contained in said cooled water tank.

14. A solar powered water collection, treatment and dispenser system comprising:
a housing assembly having a front, back, top and bottom, and a plurality of compartments at least partially enclosed therein;
a solar power assembly having at least one solar collection panel mounted to said top of said housing assembly to generate electrical power to operate said system;
a collection assembly having an air intake unit mounted through a portion of said housing assembly to draw in the surrounding moisture laden air;
said collection assembly further comprising a dehumidifier unit mounted in one of said plurality of compartments of said housing assembly to condense untreated water from the moisture laden air drawn in through said air intake unit;
a reverse osmosis assembly mounted in one of said plurality of compartments of said housing assembly and disposed in communication with said collection assembly to remove contaminants from the untreated water condensed by said dehumidifier unit to produce treated water, said reverse osmosis assembly having a primary reverse osmosis unit and a secondary reverse osmosis unit arranged in a series configuration;
said reverse osmosis assembly further comprising a contaminant meter disposed to monitor a level of contaminants remaining in the treated water discharged from said primary reverse osmosis unit and/or said secondary reverse osmosis unit;
a recirculation assembly comprising a control valve unit operable to recirculate the treated water discharged from said reverse osmosis assembly back to said primary reverse osmosis unit if the level of contaminants remaining in the treated water is above a predetermined contaminant limit;
a hot water assembly having a heated water tank mounted in one of said plurality of compartments of said housing assembly which receives treated water from said reverse osmosis assembly and dispenses hot treated water to the user therefrom via a hot water dispenser; and
a cold water assembly having a cooled water tank mounted in one of said plurality of compartments of said housing assembly which receives treated water from said reverse osmosis assembly and dispenses cold treated water to the user therefrom via a cold water dispenser;
wherein said control valve unit is further operable to discharge treated water from said reverse osmosis assembly to said cooled water tank; and
wherein said cold water assembly comprises a cooled water tank gauge to monitor a volume of treated water in said cooled water tank, said cooled water tank gauge communicative with said control valve unit to discontinue discharge of treated water from said reverse osmosis assembly to said cooled water tank when a predetermined volume of treated water is detected in said cooled water tank.

\* \* \* \* \*